United States Patent [19]

Imamura et al.

[11] Patent Number: 5,162,201

[45] Date of Patent: Nov. 10, 1992

[54] ANALYTICAL METHOD MAKING USE OF MONOGLYCERIDE LIPASE

[75] Inventors: Shigeyuki Imamura; Mamoru Takahasi; Hideo Misaki; Kazuo Matsuura, all of Shizuoka, Japan

[73] Assignee: Toyo Jozo Co., Ltd., Shizuoka, Japan

[21] Appl. No.: 668,169

[22] Filed: Mar. 12, 1991

Related U.S. Application Data

[62] Division of Ser. No. 171,272, Mar. 21, 1988, Pat. No. 5,079,158.

[30] Foreign Application Priority Data

Apr. 1, 1987 [JP] Japan ................................. 62-80299

[51] Int. Cl.$^5$ .................... C12Q 1/44; C12Q 1/26; C12Q 1/28; C12P 7/64; C12N 9/18
[52] U.S. Cl. ...................................... 435/19; 435/25; 435/28; 435/134; 435/197
[58] Field of Search .................... 435/134, 19, 25, 28, 435/198, 197, 252.5, 832

[56] References Cited

U.S. PATENT DOCUMENTS

| | | | |
|---|---|---|---|
| 3,898,130 | 8/1975 | Komatsu | 435/19 |
| 4,275,081 | 6/1981 | Coleman et al. | 435/134 |
| 4,384,042 | 5/1983 | Miike et al. | 435/19 |
| 4,491,631 | 1/1985 | Imamura et al. | 435/193 |

Primary Examiner—Douglas W. Robinson
Assistant Examiner—T. J. Reardon
Attorney, Agent, or Firm—Oblon, Spivak, McClelland, Maier & Neustadt

[57] ABSTRACT

Disclosed herein is a novel monoglygeride lipase at least capable of catalyzing an enzymatic reaction of the following equation (a) and as substrate specificity, capable of acting on monoglyceride but incapable of acting on diglyceride and triglyceride:

$$\text{Monoglyceride} + H_2O \rightarrow \text{Glycerol} + \text{Fatty acid} \quad (a)$$

The monoglyceride lipase is produced by culturing a specific monoglyceride lipase producing microorganism of Bacillus and then collecting the monoglyceride lipase from the resulting culture. A method is also disclosed for the analysis of a monoglyceride-containing sample solution. The monoglyceride lipase is caused to act on the sample solution upon measurement of the monoglyceride in the sample solution. Either one of glycerol and the fatty acid formed in accordance with the equation (a) is then measured.

21 Claims, 3 Drawing Sheets

ANALYTICAL METHOD MAKING USE OF MONOGLYCERIDE LIPASE

This is a division, of application Ser. No. 07/171,272, filed on Mar. 21, 1988, now issued as U.S. Pat. No. 5,079,158.

BACKGROUND OF THE INVENTION

1) Field of the Invention

This invention relates to a novel monoglyceride lipase, its production process and an analytical method making use of the novel monoglyceride lipase, as well as an analytical method of the enzymatic activity of pancreatic lipase.

2) Description of the Related Art

The monoglyceride lipase, which has conventionally been known to exist in a wide range of organisms ranging from microorganisms to higher animals, is known to act not only on monoglyceride but also on diglyceride and triglyceride ["KOSO HANDBOOK (Enzyme Handbook)", page 424; published Dec. 1, 1982 by The Asakura Shoten K.K.]. As another monoglyceride lipase, is known that derived from certain microorganism strains of Staphyrococcus (Japanese Patent Laid-Open No. 42532/1980). This enzyme also acts as its substrate specificity on triglyceride in addition to monoglyceride and has the following physical and chemical properties. Its optimum pH is pH 11. As its optimum temperature, it shows high activity in a range of 37°-50° C., with the activity peak located around 37°-40° C., when "Ediol" (trade mark; coconut oil emulsion) is used as a substrate. Its isoelectric point is 2.56, while its molecular weight is about 174,000. Further, it is inactivated rapidly at 55° C. and higher and its inactivation at 70° C. takes place in 10 minutes. On the other hand, known analytical methods for the activity of lipase include turbidimetric method using of triolein emulsion, the colorimetric method using a synthetic substrate (Japanese Patent Laid-Open No. 254,197/1986), the titration method in which a liberated fatty acid is titrated, the enzymatic measurement method of a fatty acid formed by using 1,2-diglyceride, a natural substrate, in the form of a synthetic substrate (Japanese Patent Laid-Open Nos. 888/1983 and 91,898/1984), etc.

Since conventional monoglyceride lipases act not only monoglyceride but also diglyceride and triglyceride as mentioned above, they cannot be used, for example, for a method of measuring only monoglyceride liberated from a synthesized substrate in the measurement method of the activity of lipase. Further, the monoglyceride lipase from the microorganism strains of Staphyrococcus cannot be used either, because it also acts on triglyceride, its molecular weight and optimum pH are high, and it is unstable under heat.

SUMMARY OF THE INVENTION

With the foregoing problems in view, the present inventors have carried out an extensive investigation. As a result, it has been found that a microorganism strain of Bacillus, H-165, isolated from soil near the hot spring of the spa of Kirishima, Kagoshima-ken, Japan produces a novel monoglyceride lipase (may hereinafter be called "the monoglyceride lipase of this invention") at least capable of catalyzing an enzymatic reaction of the following equation (a) and as substrate specificity, capable of acting on monoglyceride but incapable of acting on diglyceride and triglyceride:

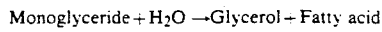

It has also been uncovered as a result of purification of the enzyme that the monoglyceride lipase produced by Bacillus stearothermophilus H-165 has excellent and absolutely novel enzymatic effects of acting on monoglyceride but not acting on diglyceride and triglyceride as its substrate specificity. It has also been revealed that the monoglyceride lipase is a heat resistant enzyme which has an optimum pH around pH 5, shows the maximum activity at an optimum temperature of 75° C., has isoelectric point 4.6 and molecular weight as low as 27,000 respectively, is not inactivated at 70° C. to any substantial extent, and still has 20% of its activity even after treatment at 90° C. The monoglyceride lipase has hence been found to be an enzyme which is novel and is useful in the method for the measurement of monoglyceride.

The present invention has been completed on the basis of the findings described above. This invention therefore relates to a novel monoglyceride lipase at least capable of catalyzing an enzymatic reaction of the below-described equation (a) and as substrate specificity, capable of acting on monoglyceride but incapable of acting on diglyceride and triglyceride; a process for the production of a novel monoglyceride lipase, which comprises culturing in a medium a monoglyceride lipase producing microorganism of Bacillus, which is at least capable of catalyzing an enzymatic reaction of the below-described equation (a) and as substrate specificity, capable of acting on monoglyceride but incapable of acting on diglyceride and triglyceride, and then collecting the monoglyceride lipase from the resulting culture; an analytical method for a monoglyceride-containing sample solution, which comprises causing a monoglyceride lipase, which is at least capable of catalyzing an enzymatic reaction of the below-described equation (a) and as substrate specificity, capable of acting on monoglyceride but incapable of acting on diglyceride and triglyceride, to act on monoglyceride upon measurement of the monoglyceride in the sample solution, and then measuring either one of glycerol and a fatty acid formed in the reaction; as well as a measurement method for the activity of pancreatic lipase in a sample solution, which comprises causing the pancreatic lipase of the sample solution to act on a reagent containing at least 1,2-diglyceride to liberate monoglyceride; causing a monoglyceride lipase, which is at least capable of catalyzing an enzymatic reaction of the below-described equation (a) and as substrate specificity, capable of acting on monoglyceride but incapable of acting on diglyceride and triglyceride, to act on the thus-liberated monoglyceride; and then measuring either one of glycerol and a fatty acid formed as components of the monoglyceride in the preceding reaction.

Owing to its substrate specificity, the monoglyceride lipase of this invention acts on monoglyceride only. In addition, its molecular weight and optimum pH are 27,000±2,700 and pH 5 respectively. It shows the maximum activity at the optimum temperature of 75° C. It is stable at pH 7-8. Its isoelectric point is pH 4.6±−0.4. It is thermally stable up to 70° C. It is hence useful for various analyses, for example, the analysis of monoglyceride contained in a beverage, food, body fluid or the like and the measurement of the activity of pancreatic lipase contained in a body fluid, serum or the like.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION

The novel monoglyceride lipase obtained in accordance with the present invention has the following physical and chemical properties.

(1) Effects:

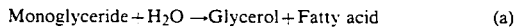

Monoglyceride + $H_2O$ → Glycerol + Fatty acid    (a)

(Monoglyceride may be either α-monoglyceride or β-monoglyceride.)

(2) Molecular weight: 27,000±2,700 [Measured using a column of a polyvinyl gel "TSK3000SW" (trade name; product of Toyo Soda Mfg., Co., Ltd.) and a 50 mM phosphate buffer (pH 6.5) containing 0.2 M of NaCl as a mobile phase.]

Figure 1:
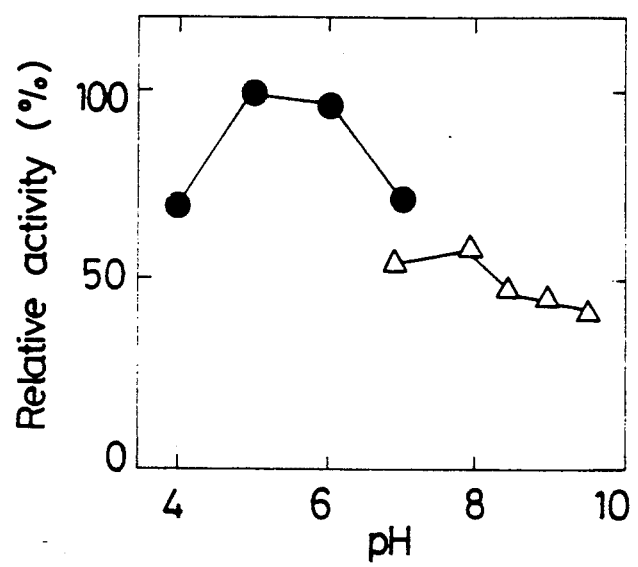
FIG. 1 shows an optimum pH curve of the monoglyceride lipase of this invention.

(3) Optimum pH: A measurement method of enzymatic activity to be described subsequently was followed. Monolaurin and the enzyme were reacted to each other for 10 minutes by separately using a dimethylglutarate buffer (pH 4–7; —●— in FIG. 1) and a tris-HCl buffer (pH 7–9.5; —△— in FIG. 1) as buffers. The reaction mixture was thereafter boiled for 2 minutes to inactivate the enzyme, thereby terminating the reaction. The reaction mixture was then incubated at 37° C., followed by enzymatic measurement of the amount of glycerin formed. Results are shown in FIG. 1. The optimum pH was around pH 5.

Figure 2:
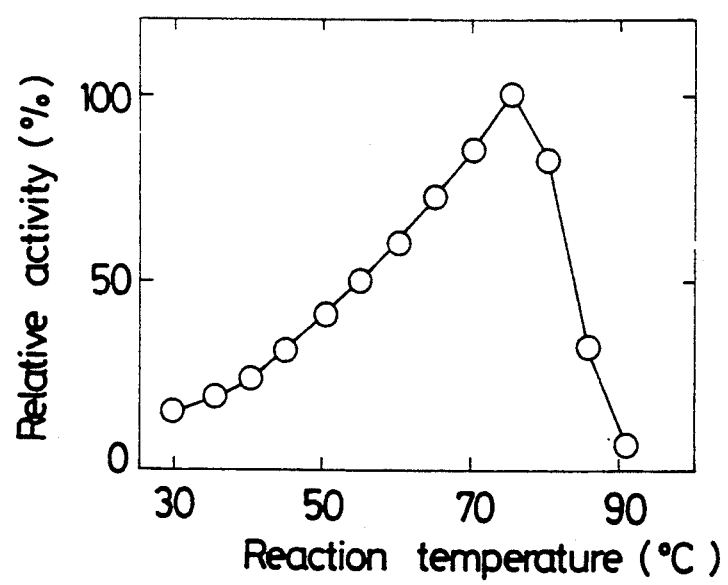
FIG. 2 shows an optimum temperature curve of the, same enzyme.

(4) Optimum temperature: Using a PIPES-NaOH buffer (pH 7.3), reactions were carried out separately at individual temperatures shown in FIG. 2. The reaction mixtures were separately boiled subsequent to their corresponding reactions. Following the below-described measurement method, the amounts of glycerin formed were separately measured. Results are shown in FIG. 2. The maximum activity was exhibited at 75° C.

Figure 3:
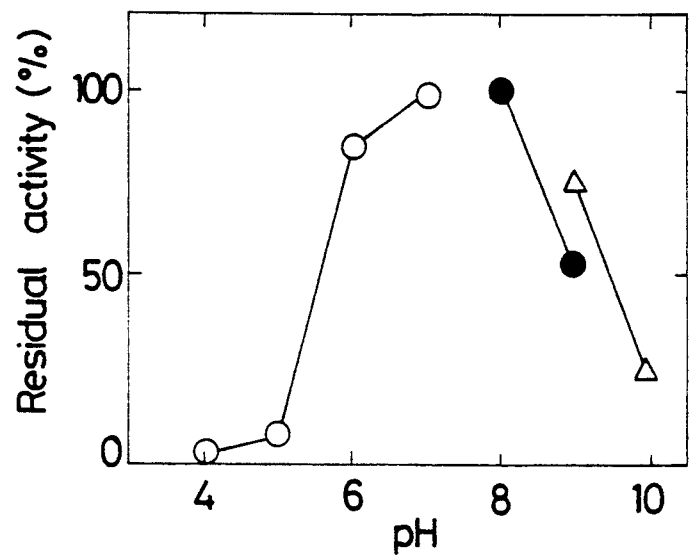
FIG. 3 shows a pH stability curve of the same enzyme.

(5) pH stability: Solutions (1.0 U/ml) of the present enzyme were separately prepared with a 10 mM dimethylglutaric acid-NaOH buffer (pH 4–7; —○— in FIG. 3), a tris-HCl buffer (pH 8–9; —●— in FIG. 3) and a glycin-NaOH buffer (pH 9–10; —△— in FIG. 3). After treating the individual solutions at 75° C. for 10 minutes, its residual activity was measured in accordance with the below-described measurement method of enzymatic activity. Results are shown in FIG. 3. The enzymatic activity remained stable in a pH range of 7–8.

Figure 4:
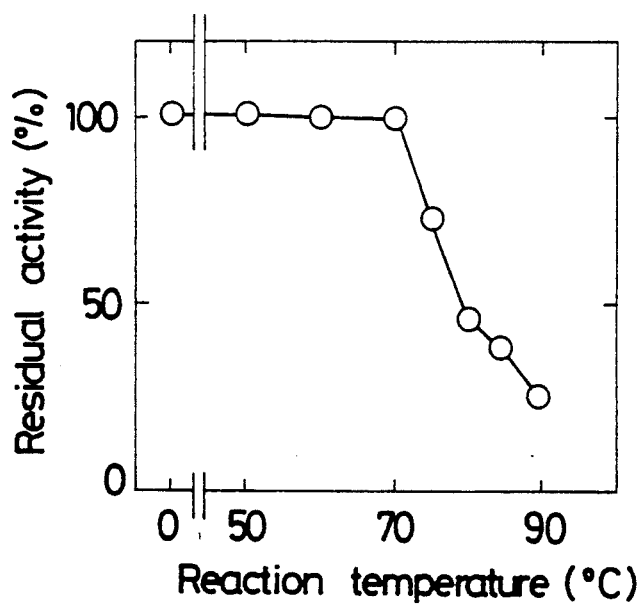
FIG. 4 shows a thermal stability curve of the same enzyme.

(6) Thermal stability: A solution (1.0 U/ml) of the present enzyme was prepared with a 10 mM tris-HCl buffer (pH 7.5). After heat treatment of portions of the solution for 10 minutes at individual temperatures shown in FIG. 4, the residual activity was measured in accordance with the below-described measurement method of enzymatic activity. Results are shown in FIG. 4. The enzymatic activity remained stable up to 70° C.

(7) Isoelectric point: pH 4.6±0.4 (After feeding a current of a constant voltage of 700 V at 4° C. for 40 hours by isoelectric focusing electrophoresis making use of an ampholyte as a carrier, the enzymatic activity of each fraction was measured.

(8) Substrate specificity: The substrate specificity of the monoglyceride lipase of this invention was investigated under conditions which followed the below-described measurement method of enzymatic activity for the monoglyceride lipase of this invention. As a result, as summarized in Table 1, the maximum activity was exhibited against α-monolaurin. When diglyceride derived from yolk lecithin, 1,2-dilinolein, 1,3-dilinolein and triolein were used as substrates, glycerol hydrolyzed from those substrates were not detected in the presence of the monoglyceride lipase of this invention. The monoglyceride lipase of the present invention has hence been regarded not to act on diglyceride and triglyceride as substrates.

Here, a description is made of the action of the monoglyceride lipase of this invention on β-monoglyceride as a substrate specificity.

1) Confirmation of a fatty acid liberated from α-linoleoyl-β-oleoyl-diglyceride as a substrate, by high performance liquid chromatography (HPLC):

i) Pancreas-derived lipase (50 μl) was added to 1.0 ml of a reaction solution having a composition of 0.5 mg of α-linoleoyl-β-oleoyl-diglyceride, 1.8 mg of a non-ionic surface active agent ("Triton X-100", trade name; product of Sigma Chemical Company), 3.8 mg of deoxycholic acid, 20 U of colipase, 0.15 mg of calcium chloride, and 200 μl of 0.1 M N-tri(hydroxymethyl) methyl-3-aminopropanesulfonic acid (TAPS)-NaOH (pH 8.3). After allowing them to react at 37° C. for 10 minutes, the reaction was terminated. A 15 μl aliquot of the reaction mixture was applied on a column and was then analyzed by high performance liquid chromatography under the following conditions.

Column: "Zorbox ODS" (trade name; 4.6 mmφ×25 cm)
Solvent: acetonitrile:$H_2O$ (96:4)
Detection: ultraviolet absorption at 205 nm
Flow rate: 1.2 ml/min As a result, linoleic acid was detected at the retention time of 23 minutes but no oleic acid was detected. In view of the detection of the linoleic acid bound at the α-position same as 1 position, pancreatic lipase has been found to act on the α-position of α,β-diglyceride same as 1,2-position as a substrate and to hydrolyze the same position. The formation of β-oleoyl-monoglyceride has also been gathered.

ii) The monoglyceride lipase (0.5 U) was added to a reaction solution of the same composition as that employed above. A fatty acid liberated in substantially the same manner was detected by high performance liquid chromatography. As a result, linoleic acid and oleic acid were confirmed at the retention times of 23 minutes and 31 minutes respectively. From these results, it has been found that the monoglyceride lipase of this invention acts on the substrate, namely, β-monoglyceride same as 2-position formed by pancreatic lipase from α,β-diglyceride and liberates the oleic acid bound at the β-position. Glycerol liberated from α,β-diglyceride was hence detected.

2) Substrate specificity of the monoglyceride lipase upon use of α,β-diglyceride as a substrate:

i) The below-described α,β-diglycerides were separately employed as substrates. Their α-positions were hydrolyzed by using pancreatic lipase and the monoglyceride lipase of this invention was caused to act on β-monoglycerides thus formed. Thereafter, glycerol thus liberated was analyzed. As a result, glycerol was detected with respect to all the substrates, namely, α-oleyl-β-palmitoyldiglyceride, α-palmitoyl-β-oleoyldiglyceride and α,β-dilinoleylglyceride.

Incidentally, glycerol was not detected when pancreatic lipase was used singly.

(9) Effects of surface active agent and metal ions: When surface active agents such as "Triton X-100" (trade name) and cholic acid were added, inhibition of the activity is observed in a high concentration range. The monoglyceride lipase of this invention is not affected by the addition of divalent metal ions such as $Ca^{++}$ and $Mg^{++}$.

TABLE 1

Substrate Specificity of the Monoglyceride Lipase

| Substrate | Activity of lipase (%) |
|---|---|
| α-monoglyceride: | |
| Monoacetin | 10.1 |
| Monobutyrin | 47.1 |
| Monocaprin | 89.1 |
| Monolaurin | 100.0 |
| Monomyristin | 85.7 |
| Monopalmitin | 39.5 |
| Monoolein | 56.3 |
| β-monoglyceride: | |
| Monoolein | 75.6 |
| Diglycerides: | |
| Derived from yolk lecithin* | 0 |
| 1,2-dilinolein | 0 |
| 1,3-dilinolein | 0 |
| Triglyceride: | |
| Triolein | 0 |

*Preparation method: Phospholipase C was caused to act on purified yolk lecithin. Fractions extracted by chloroform-methanol was used.

TABLE 2

Effects of Surface Active Agents and Metal Ions on the Monoglyceride Lipase

| Reagent | Concentration | Activity of lipase (%) |
|---|---|---|
| Not added | — | 100 |
| Triton X-100 | 0.1% | 81.7 |
| Triton X-100 | 0.5% | 46.5 |
| Cholic acid | 1 mM | 100.0 |
| Cholic acid | 10 mM | 92.6 |
| $CaCl_2$ | 1 mM | 100.0 |
| $MgCl_2$ | 1 mM | 100.0 |
| EDTA | 1 mM | 86.0 |

<Measurement Method of Enzymatic Activity>

| | |
|---|---|
| 0.2 M PIPES-NaOH buffer (pH 7.3) | 0.1 ml |
| 0.3% 4-Aminoantipyrine | 0.05 ml |
| 0.2% TOOS** | 0.05 ml |
| (45 U/ml) Peroxidase | 0.05 ml |
| 20 mM $MgCl_2$ | 0.025 ml |
| 20 mM ATP | 0.025 ml |
| (25 U/ml) Glycerol kinase | 0.01 ml |
| (1000 U/ml) glycerophosphoric acid oxidase | 0.015 ml |

TABLE 2-continued

| | |
|---|---|
| Purified water | 0.075 ml |

(**TOOS: N-ethyl-N-(2-hydroxy-3-sulfopropyl)-metha-toluidine)

To 0.4 ml of a reaction solution of the above composition, 50 μl of 10 mM monolaurin (0.5% aqueous solution of "Triton X-100") was added. The resultant mixture was provisionally heated at 37° C. for 2–3 minutes and 50 μl of an enzyme solution was added to initiate a reaction. Exactly 10 minutes later, 2.5 ml of 0.5% SDS (sodium dodecyl suflate) was added to terminate the reaction. The absorbance was measured at a wavelength of 550 nm. Regarding the enzymatic activity, the activity capable of producing 1 μmole of glycerol per minute was defined as 1 Unit (1 U). The following equation will be followed upon calculation of enzymatic activity (potency) by this measurement method of enzymatic activity.

$$\text{Enzymatic activity(U/ml)} = \Delta A\ 550 \times \frac{2.95}{18.0} \times \frac{1,000}{50} \times \frac{1}{10}$$

ΔA 550: Absorbance at the wavelength of 500 nm
2.95: Total volume of reaction mixture (ml)
18.0: Millimolar extinction coefficient of hydrogen peroxide ($cm^2$/μmole)
50: Volume of enzyme solution used (μl)
10: Reaction time (min)

Next, *Bacillus stearothermophilus* H-165 strain, one example of microorganisms capable of producing the monoglyceride lipase of this invention, has the following mycological characteristics.

A. VISUAL OBSERVATION

The following results were obtained upon culturing at 50°–55° C. for 18–44 hours.

(1) Nutrient agar slant culture:
Presents a gray white color tinged in a yellow color. Grows in the form of lines. The growth is good and no soluble pigment is produced.

(2) Nutrient agar flat culture:
Shows a gray color tinged in a yellow color. A circular flat entire colony is formed but no soluble pigment is produced.

(3) Liquid medium:
Good growth is observed. The medium becomes turbid uniformly.

(4) BCP milk medium:
The medium remains unchanged.

B. MORPHOLOGICAL CHARACTERISTICS (1) Shape and arrangement:
The strain is a cylindrical bacillus which is either straight or is slightly bent at one or both ends. Cells are either discrete or bound together two by two. Short chains may be formed occasionally.

(2) Size:
0.6–0.8 × 2.5–4.0 μm.

(3) Mobility:
None.

(4) Spore:
A spore in the shape of an egg or an elongated circle is found at a central part of each cell or at a location close to the contour of each cell. Its size is 0.8–1.2 × 1.5–2.0 μm. The cell expands by the spore.

(5) Polymorphism:
None.

| C. Physiological and biochemical characteristics: | |
|---|---|
| Gram stain | + |
| KOH Reaction | − |
| Acid-fast stain | − |
| Capsule formation | − |
| OF test (Hugh-Leifson medium) | No changes |
| OF test (modified medium)*** | 0 (oxidized) |
| Growth under anaerobic conditions | − |
| Growth temperature | |
| 60° C. | ± |
| 50° C. | + |
| 47° C. | + |
| Growth pH | |
| 8.6 | − |
| 7.7 | + |
| 5.6 | + |
| 4.4 | − |
| Salt resistance | |
| 0% | + |
| 3% | + |
| 5% | − |
| Hydrolysis of gelatin | − |
| Hydrolysis of starch | + |
| Hydrolysis of casein | − |
| Hydrolysis of aesculin | + |
| Hydrolysis of cellulose | − |
| Hydrolysis of arginin | + |
| Production of catalase | + |
| Production of oxidase | + |
| Production of urease (SSR medium) | − |
| Production of urease (Chris medium) | + |
| Production of indole | − |
| Production of hydrogen sulfide | − |
| Production of acetoin | − |
| MR test | − |
| Reduction of nitrates | + |
| Denitrification | − |
| ***Medium composition: | |
| (NH$_4$)$_2$HPO$_4$ | 1.0 g |
| MgSO$_4$·7H$_2$O | 0.2 g |
| Glucose | 10.0 g |
| BTB (0.2% aq. soln.) | 10.0 g |
| KCl | 0.2 g |
| Yeast extract | 1.0 g |
| Agar | 3.0 g |
| Distilled water (pH 7.0) | 1000.0 ml |
| Assimilation test (Simons medium): | |
| Citric acid salts | − |
| Maleic acid salts | − |
| Malic acid salts | + |
| Gluconic acid salts | + |
| Propionic acid salts | − |
| Malonic acid salts | − |
| Succinic acid salts | + |
| Assimilation test (Christensen medium): | |
| Citric acid salts | + |
| Maleic acid salts | − |
| Malic acid salts | + |
| Gluconic acid salts | + |
| Propionic acid salts | + |
| Malonic acid salts | − |
| Succinic acid salts | + |
| Production of gas from glucose | − |
| Production of acids from sugars [(NH$_4$)$_2$HPO$_4$ was used as an N source] | |
| Adonitol | − |
| L(+)-Arabinose | − |
| Cellobiose | + |
| Dulcitol | − |
| Meso-erythritol | − |
| Fructose | + |
| Galactose | − |
| Glucose | + |
| Glycerin | + |
| Inositol | − |
| Inulin | − |
| Lactose | − |
| Maltose | + |
| Mannitol | + |
| Mannose | + |
| Melezitose | + |
| Melibiose | + |
| Raffinose | + |
| L(+)-Rhamnose | − |
| D-Ribose | + |
| Salicin | + |
| Sorbitol | − |
| Sorbose | − |
| Starch | + |
| Sucrose | + |
| Trehalose | + |
| Xylose | + |

From the mycological characteristics described above, the strain H-165 may be defined as a thermophilic temperature aerobic bacterium which is a non-mobile cylindrical bacillus having a straight shape or slightly bent end or ends, is gram-positive, has a size of 0.6–0.8×2.5–4.0 μm, forms a spore and undergoes cell expansion by the spore, decomposes glucose oxidatively and produces an acid, and is positive in the catalase and oxidase productivity. The strain having such various characteristics is judged to fall within the family of Bacillus, because it is a spore-forming, gram-positive, aerobic and rod-shaped bacterium. As other microorganism strains showing the same characteristics as the above strain with respect to acetoin productivity, indole productivity, gas productivity from glucose and growing ability under anaerobic conditions, may be mentioned (A) *Bacillus stearothermophilus*, (B) *Bacillus alcalophilus*, (C) *Bacillus badius* and (D) *Bacillus firmus*. The mycological characteristics of these bacterium species and those of the strain of this invention can be compared as follows [+: positive, −: negative, d: different depending on strains, ND: no available data].

| | A | B | C | D | Strain of this invention |
|---|---|---|---|---|---|
| Gram stain | + | + | + | + | + |
| Cell expansion by spore | d | − | − | − | + |
| Anaerobic growth | − | − | − | − | − |
| Catalase production | + | + | + | + | + |
| Gelatin hydrolysis | + | + | ND | + | − |
| Starch hydrolysis | + | + | − | + | + |
| Casein hydrolysis | d | + | + | + | − |
| Indole production | − | − | − | − | − |
| Acetoin production | − | − | − | − | − |
| Reduction of nitrates | d | − | − | d | + |
| Assimilation of citric acid salts | d | − | − | − | − |
| Production of gas from glucose | − | − | − | − | − |
| Production of acid from L-arabinose | d | + | − | − | − |
| Production of acid from D-glucose | + | + | − | + | + |
| Production of acid from mannitol | d | + | − | + | − |
| Production of acid from D-xylose | d | + | − | − | + |
| Growth at 60° C. | + | − | − | − | + |

From the above comparison, the characteristics of the strain of this invention was found to conform very well with those of *Bacillus stearothermophilus* except for gelatin degradability. Therefore, the strain of this invention was identified to belong to *Bacillus stearothermophilus*, named *Bacillus stearothermophilus* H-165, and deposited under FERM BP-1673 with Fermentation Research Institute, Agency of Industrial Science and Technology, Ministry of International Trade and Industry, the Government of Japan.

The above-described *Bacillus stearothermophilus* H-165 is merely one example of monoglyceride lipase producing microorganisms of Bacillus useful in the practice of this invention. The present invention is not limited to the use of this particular strain and microorganisms capable of producing the monoglyceride lipase of this invention can all be used in the present invention.

Upon production of the monoglyceride lipase of this invention, a microorganism capable of producing the monoglyceride lipase of this invention can be cultured by a method employed routinely in the production of antibiotics, enzymes and the like. The style of the culture may be either liquid culture or solid culture. For industrial application, it is desirable to inoculate cells of a monoglyceride lipase producing microorganism in a productive medium and then to subject the cells to submerged aerated-stirring culture.

As nutrient sources for the medium, various nutrient sources employed generally for the culture of microorganisms may used. As a carbon source, any carbon compound may be used so long as it is assimilable. It is hence possible to use, for example, carbohydrates such as glucose, sucrose, lactose, galactose, maltose, mannitol, sorbitol, dextrin and starch, various organic acids, vegetable oils such as soybean oil and olive oil, animal oils and fats such as lard and fowl oil, etc. As a nitrogen source, any nitrogen compound may be employed so long as it is assimilable. For example, peptone, powdered yeast extract, meat extract, soybean flour, casein, defatted cotton seed flour or the like may be used. In addition, one or more of various salts such as phosphates, magnesium salts, calcium salts, potassium salts, sodium salts, zinc salts, iron salts, manganese salts and halogen salts, corn steep liquor, various vitamins and the like may also be used as needed.

The culture temperature may be varied suitably within a temperature range in which a microorganism capable of producing the monoglyceride lipase of this invention can grow and produces the enzyme of this invention. The preferable culture temperature may however be 40°–65° C., especially, 45°–50° C. Although the culture time varies depending on the culture conditions, it is only necessary to terminate the culture at a suitable time point by watching the timing at which the enzyme of this invention reaches the maximum potency. The preferable culture time may be 10–22 hours.

The monoglyceride lipase of this invention is then prepared from the thus-obtained culture of the monoglyceride lipase producing microorganism. Since the enzyme of this invention is contained in its cells, the cells are collected from the culture by such a method as filtration or centrifugation. These cells are then disrupted by choosing and combining various cell-disrupting methods such as mechanical disrupting methods, e.g., ultrasonication, processing by a French press and processing by glass beads, and enzymatic disrupting methods, e.g., lysozyme treatment, whereby a crude solution containing the monoglyceride lipase of this invention is obtained. A surface active agent such as "Triton X-100" (trade name) may also be added as needed.

The monoglyceride lipase of this invention can next be obtained in a purified form from the crude solution by using a known isolation and purification method for proteins, enzymes and the like. The enzyme of this invention may be recovered, for example, by fractional precipitation or salt fractionation. The former method comprises adding an organic solvent such as acetone, methanol, ethanol or isopropanol to the crude enzyme solution containing the monoglyceride lipase of this invention, while the latter method comprises adding ammonium sulfate, sodium chloride, sodium sulfate or the like to the crude enzyme solution. The resultant precipitate may then be purified by one or more of various chromatographic methods such as molecular sieve chromatography and further by electrophoresis, ultracentrifugation or the like until a single peak is indicated. As these purification methods, it is necessary to choose purification methods which make use of properties of the intended monoglyceride lipase of this invention. For example, after dissolving the above precipitate in water or a buffer and if necessary, dialyzing the resulting solution through a semipervious membrane, the solution or dialyzate is subjected to ion-exchange chromatography on an anion-exchange resin such as DEAE-cellulose, DEAE-"Sephacel" (trade mark), DEAE-"Sepharose" (trade mark), DEAE-"Sephadex A-50" (trade name) or DEAE-"Toyo Pearl" (trade mark) or a gel filtration medium such as "Sephadex G-100" (trade name), "Sephadex G-75" (trade name) or "Sephacryl S-200" (trade name). After suitably applying two or more of these methods in combination, the monoglyceride lipase of this invention is purified by electrophoresis, ultracentrifugation or the like until a single peak is indicated. A stabilizer such as sugar, for example, mannitol, sucrose or sorbitol, an amino acid such as glutamic acid or glycin, or a peptide or protein such as bovine serum albumin is then added, followed by further processing such as lyophilization to obtain powder of the enzyme of this invention in a purified form.

As has been described above, the monoglyceride lipase of this invention is at least capable of catalyzing the enzymatic reaction of the below-described equation (a) but incapable of catalyzing the enzymatic reactions of the below-described equations (b) and (c) and as substrate specificity, capable of acting on monoglyceride but incapable of acting diglyceride and triglyceride. In addition, its molecular weight and optimum pH are 27,000±2,700 and pH 5 respectively. It shows the maximum activity at the optimum temperature of 75° C. It is stable at pH 7–8. Its isoelectric point is pH 4.6±−0.4. It is thermally stable up to 70° C. From these chemical and physical properties, the monoglyceride lipase of this invention has been recognized to be different from the known monoglyceride lipases. It is accordingly clear that the monoglyceride lipase of this invention is a novel enzyme.

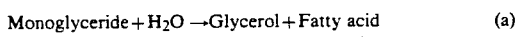

Monoglyceride + H₂O → Glycerol + Fatty acid        (a)

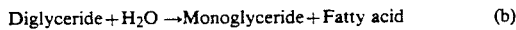

Diglyceride + H₂O → Monoglyceride + Fatty acid     (b)

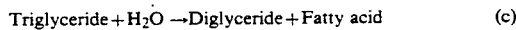

Triglyceride + H₂O → Diglyceride + Fatty acid      (c)

Further, a sample solution containing monoglyceride can be analyzed by causing the novel enzyme of this invention, i.e., the monoglyceride lipase of this invention to act on the monoglyceride in the sample solution and then measuring either one of the resulting glycerol or fatty acid. The novel analytical method of monoglyceride is useful as various analytical methods such as the analysis of monoglyceride contained in beverages, foods, body fluids and the like and the measurement of the activity of pancreatic lipase contained in body fluids, serum and the like.

Namely, this invention provides an analytical method for a monoglyceride-containing sample solution, which comprises causing a monoglyceride lipase, which is at least capable of catalyzing an enzymatic reaction of the below-described equation (a) but incapable of catalyzing enzymatic reactions of the below-described equations (b) and (c) and as substrate specificity, capable of acting on monoglyceride but incapable of acting on diglyceride and triglyceride, to act on monoglyceride, and then measuring either one of glycerol and a fatty acid formed as components of monoglyceride in the reaction.

Monoglyceride + H₂O → Glycerol + Fatty acid (a)

Diglyceride + H₂O → Monoglyceride + Fatty acid (b)

Triglyceride + H₂O → Glyceride + Fatty acid (c)

No particular limitation is imposed on the monoglyceride-containing sample solution in the present invention, so long as monoglyceride is contained as a substrate for the novel enzyme, i.e., the monoglyceride of this invention. It may be a monoglyceride-containing sample solution obtained from a beverage or food. As an alternative, it may be a sample solution which contains monoglyceride formed by adding 1,2-diglyceride to a sample solution of pancreatic lipase and then conducting a reaction under certain specific conditions for measuring the activity of pancreatic lipase. A method for measuring the activity of pancreatic lipase by combining 1,2-diglyceride as a substrate for pancreatic lipase and the monoglyceride lipase of this invention may be mentioned by way of example, in which 1,2-diglyceride as the substrate for pancreatic lipase and a nonionic surface active agent are added to a pancreatic lipase containing body fluid as a sample solution, a reaction is induced under certain specific reaction conditions to form monoglyceride from the substrate, i.e., 1,2-glyceride; by the action of pancreatic lipase, the monoglyceride lipase of this invention is caused to act on the thus-formed monoglyceride, and either one of glycerol and a fatty acid thus formed as components of the monoglyceride is quantitatively analyzed. As additives which may be added to enhance the action of pancreatic lipase upon measurement of the activity of pancreatic lipase in the reaction sample solution, there are colipase, sodium deoxycholate, calcium chloride, ammonium chloride and the like by way of example. Further, sodium cholate or the like may be mentioned as a solubilizer for the substrate.

The monoglyceride lipase useful in the measurement of the activity of pancreatic lipase is the novel enzyme of this invention as described above. It may be used in an amount sufficient to hydrolyze monoglyceride to be formed by the pancreatic lipase in the sample solution. It is generally sufficient to use it in an amount of 0.1 U/ml or greater, with about 0.5–2 U/ml being preferred. The enzyme of this invention employed here may be either still in the form of the aqueous solution of in a form added with a buffer. As an alternative, it may also be used in a lyophilized form.

In the manner as described above, the monoglyceride lipase of this invention is caused to act on monoglyceride and is then incubated for a predetermined period of time. The reaction time and reaction temperature may be such that would allow the enzyme to react sufficiently. For example, the reaction temperature may be 30°–40° C., preferably, around 37° C. As a result of this reaction, glycerol and a fatty acid are formed in the sample solution and either one of these glycerol and fatty acid is then measured.

For the measurement of glycerol, use of an enzyme capable of acting on glycerol as a substrate, for example, glycerokinase.glycerophosphate oxidase method or glycerol oxidase method is simple and effective. For example, in the former method, glycero-3-phosphate formed from glycerol by using ATP and a glycerokinase is oxidized by glycerophosphate oxidase. In the glycerokinase.glycerophosphate oxidase method, 0.1–10 U/ml of glycerokinase, 0.1–2.0 mM adenosine triphosphate (ATP) and 2–50 mM of magnesium chloride are added to glycerol formed from monoglyceride by the monoglyceride lipase of this invention, whereby adenosine diphosphate (ADP) and glycero-3-phosphate are formed. By causing 2.0–50 U/ml of glycerophosphate oxidase to act on glycero-3-phosphate thus formed, oxygen is consumed to form dihydroxyacetonephosphate and hydrogen peroxide. The glycerol may then be determined quantitatively by measuring the oxygen consumed in the reaction mixture or either one of the dihydroxyacetone-phosphate and hydrogen peroxide formed in the reaction mixture. For the measurement of the consumed oxygen, use of oxygen electrodes is simple and easy. As a method for the measurement of the resultant hydrogen peroxide, may be mentioned a method making use of hydrogen peroxide electrodes, a colorimetric method making use of a dye composition containing one or more chromogen reagents which undergo absorbance changes upon reaction with hydrogen peroxide, or the like. As illustrative examples of such chromogen reagents, may be mentioned those making use of a reaction between a tetravalent titanium compound, which is capable of forming a stable red substance upon reaction with the resulting hydrogen peroxide, and xylenol orange, a reaction between N-ethyl-N-(2-hydroxy-3-sulfopropyl)-methatoluidine (hereinafter abbreviated as "TOOS") or phenol, 4-aminoantipyrine and peroxidase, or the like. In the reaction between TOOS or phenol, 4-aminoantipyrine and peroxidanse, phenol or TOOS may be used in an amount of about 0.01–0.1% based on the whole solution. On the other hand, 4-aminoantipyrine may be used in an amount of 0.01–0.1%, preferably, 0.03% based on the amount of the resultant hydrogen peroxide, while peroxidase may be used in an amount of 0.5–10 U/ml. The thus-prepared chromogen reagent may also be prepared together with the monoglyceride lipase of this invention. Thereafter, the Quinoneimine dye produced as a result of the color reaction is measured at a suitable wavelength. The hydrogen peroxide may then be analyzed quantitatively from a calibration curve. Furthermore, a fluorescent substance such as homovanillic acid may be used in place of the above-described chromogen reagent.

Similarly, 5–50 U/ml of glycerol oxidase is caused to act on the glycerol formed as mentioned above in the glycerol oxidase method so that oxygen is consumed and dihydroxyacetone and hydrogen peroxide are formed. It is then only necessary to measure the amount of the thus-formed hydrogen peroxide in the same manner as in the measuring method for the amount of oxygen or hydrogen peroxide in the glycerokinase. glycerophosphate oxidase method. Further, as a method for the quantitative analysis of glycerol, reduced NAD formed by using glycerophosphate dehydrogenase instead of the above-mentioned glycerophate oxidase may be analyzed by a quantitative analytical method known to date. ADP formed from ATP upon action of glycerokinase on ATP may be measured in accordance with a known method.

Further, in the measurement of activity of pancreatic lipase for example, 1,2-diglyceride capable of serving as a substrate for pancreatic lipase, a non-ionic surface active agent, an additive for enhancing the effects of pancreatic lipase activity, a solubilizer for the substrate, an additive for promoting the reaction for the formation of glycerol and a fatty acid from monoglyceride, an enzyme for measuring glycerol thus formed and an additive for enhancing the action of the enzyme, a chromogen reagent for the measurement of hydrogen peroxide formed, etc. may be formulated along with the monoglyceride lipase of this invention. The kinds and amounts of the substrate, i.e., 1,2-diglyceride and surface active agent usable in the measurement of activity of pancreatic lipase may be suitably chosen with reference to Japanese Patent Laid-Open No. 91,898/1984, corresponding to U.S. application Ser. No. 06/554,028, whose continuation-in-part and continuation applications matured into U.S. Pat. No 4,845,028. In the Rate assay as a method for the measurement of the activity of pancreatic lipase, 30 μl of a sample (serum) provided for the measurement of the activity of pancreatic lipase is caused to act on 1.5 ml of a reaction solution prepared in advance and the reaction mixture is then subjected to continuous colorimetric measurement at 37° C. (or 30° C. or 25° C. as an alternative) and a wavelength of 550 nm. In the End point assay, 50 μl of a sample (serum) provided for the measurement of the activity of pancreatic lipase is caused to act on 1.0 ml of a reaction solution prepared in advance and after allowing the mixture to react exactly for 30 minutes at 37° C., 1.0 ml of 0.5% SDS is added, and a colorimetric measurement is then conducted at a wavelength of 550 nm.

On the other hand, a cycling reaction may be used as a method for measuring the fatty acid. The cycling reaction comprises a reaction step of the enzyme as an initial step in which the fatty acid liberated from monoglyceride by the action of the monoglyceride lipase is converted as a starting substance to acyl-CoA, a series of several successive steps comprising a combination of several reaction steps in which an enzymatic reaction product obtained in the preceding step is used as a substrate for an enzymatic reaction in a given step so as to convert the substrate to a substrate for the enzymatic reaction in the next step, and a final step of conversion to the acyl-CoA formed in the starting step. More specifically, these steps are conversion steps to the acyl-CoA in which the fatty acid is converted to the acyl-CoA in the initial step, the acyl-CoA is converted to the dehydroacyl-CoA in the next step, the dehydroacyl-CoA is converted to the hydroxyacyl-CoA, the hydroxyacyl-CoA is converted to the ketoacyl-CoA, and the ketoacyl-CoA is finally converted to the acyl-CoA. Owing to the combination of these steps, the amount of the fatty acid can be successfully measured as a cycling reaction. Namely, the acyl group of the acyl-CoA formed in the final step of the reaction has carbon atoms the number of which is smaller by 2 compared with the chain length of the starting fatty acid of the reaction. The acyl-CoA is then converted to the dehydroacyl-CoA, hydroxyacyl-CoA and ketoacyl-CoA successively through the cycling reaction. The cycling reaction establishes such a cycle that acyl-CoA having a carbon number smaller by 2 is formed in its final step. Therefore, a cycling reaction of a high order corresponding to the number of carbons of the fatty acid takes place. By measuring the cumulative amount of a substance of a high molar ratio formed or consumed from 1 molar of fatty acid in the course of the cycling steps in accordance with various means, the cumulative amount can be measured as a variant detectable with extremely high sensitivity. This measurement includes the following reaction steps (a) through (e). (a) The fatty acid is converted to the acyl-CoA by a reaction which is based on ATP or GTP, CoASH and the activity of the acyl-CoA.synthetase. (b) The The acyl-CoA is then converted to the dehydroacyl-CoA by a reaction which is based on the oxygen and the activity of the acyl-CoA.oxidase. (c) The dehydroacyl-CoA is next converted to the hydroxyacyl-CoA by a reaction which is based on water and the activity of enoyl-CoA.hydratase. (d) The hydroxyacyl-CoA is thereafter converted to the ketoacyl-CoA and reduced NAD by a reaction which is based on NAD and the activity of the 3-hydroxyacyl-CoA.dehydrogenase. (e) Finally, the ketoacyl-CoA is converted to the acyl-CoA, whose acyl group has a carbon number smaller by 2 compared with that of the acyl group of the acyl-CoA formed in the reaction step (a), by a reaction which is based on CoASH and the activity of the 3-ketoacyl-CoA.thiolase. Namely, the thus-formed acyl-CoA is subjected to β oxidation through the reactions of the subsequent reaction steps, so that it is converted to acyl-CoA whose acyl group has a carbon number smaller by 2 compared with the first-mentioned acyl-CoA. It is hence only necessary to measure by spectrophotometry reduced NAD, which is formed and accumulated in the course of the cycling reaction, as a detectable variant of a substance formed in the reaction system. This reduced NAD may be measured by spectrophotometry at about 320-360 nm which are wavelengths not specific to NAD but specific to reduced NAD. As an alternative, the reduced NAD may be measured by colorimetry, using a chromogen which takes part in the hydrogen transport system and contains diaphorase and a water-soluble tetrazolium salt. The enzymes and reagents employed upon measurement of the fatty acid may be prepared suitably with reference to Japanese Patent Laid-Open Nos. 51899/1983 and 91898/198, corresponding to U.S. application Ser. No. 06/392,010, now U.S. Pat. Nos. 4,491,631 and 4,845,028, respectively.

The analytical method making use of the novel monoglyceride lipase of this invention produced in the above manner measures either one of the resultant glycerol and fatty acid. It is hence useful for various analyses, for example, the analysis of monoglyceride contained in a beverage, food, body fluid or the like and the measurement of the activity of pancreatic lipase contained in a body fluid, serum or the like.

This invention will hereinafter be described specifically by the following Examples. It should however be borne in mind that this invention is by no means limited by the following Examples.

EXAMPLE 1

Culture of Cells

After 100 ml of a culture (pH 7.0) containing 1.0% of peptone, 0.5% of powdered yeast extract, 1.0% of milk casein, 0.2% of NaCl, 0.1% of $K_2HPO_4$, 0.05% of $MgSO_4.7H_2O$ and 0.5% of olive oil was sterilized at 120° C. for 20 minutes, a seed culture of *Bacillus stearothermophilus* H-165 which had been cultured in advance at 50° C. for 15 hours in an agar medium of the same composition as the above culture was transplanted to the above culture. The strain was cultured under shaking at 50° C. for 25 hours. From about 10th hour, the activity of the monoglyceride lipase was observed in cells thus grown. When the activity reached the peak (0.1 U/ml), the culturing was terminated and the resultant culture was centrifuged at 3,000 rpm for 10 minutes to collect cells.

EXAMPLE 2

Extraction and Purification of Enzyme

Figure 5:
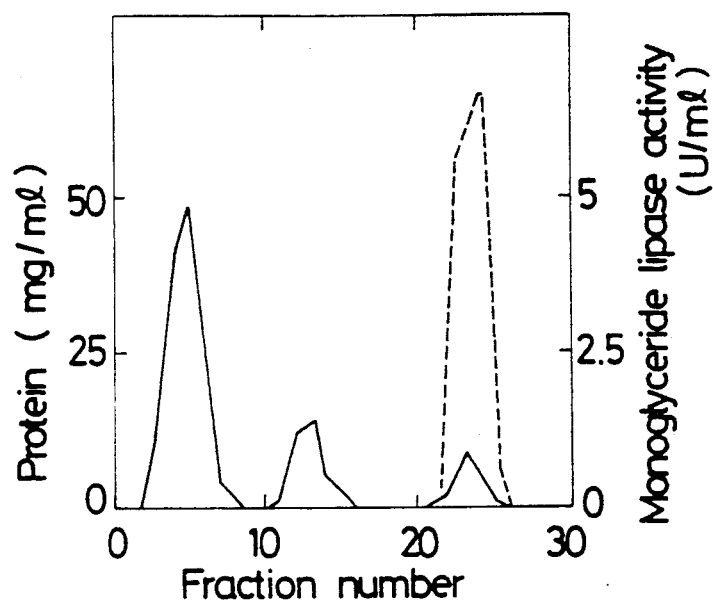
FIG. 5 shows an elution profile of the same enzyme in its purification step.

Cells, which had been collected from 1,000 ml of a culture (10 Erlenmeyer flasks of 500 ml capacity) obtained in the same manner as in Example 1, were suspended in 200 ml of a 10 mM phosphate buffer (pH 7.0) and were then subjected to ultrasonication (200 W, 10 minutes) to solubilize the enzyme. The thus-solubilized solution was centrifuged at 15,000 rpm for 10 minutes to obtain 175 ml of a clear supernatant, to which 350 ml of chilled acetone was added to precipitate the enzyme. After dissolving the precipitate in 65 ml of a 10 mM phosphate buffer (pH 7.0) containing 10% of ammonium sulfate, the resultant solution was charged in a column (3.5×5 cm) packed with "Octyl-Sepharose" (trade mark; product of Pharmacia AB) so that the enzyme was adsorbed. Components not adsorbed on the column were washed away with 50 ml of a phosphate buffer (pH 7.0) which contained 10% of ammonium sulfate. After washing the column with a 10 mM phosphate buffer (pH 7.0), the enzyme was eluted with 3% Triton X-100 from the column. The eluate was fractionated as 10 ml-fractions. Results are shown in FIG. 5. Active fractions (Nos. 22–25) were combined and then concentrated to 4 ml by an ultrafiltration membrane produced by AMICON CORP. The enzyme was then precipitated with 10 ml of chilled acetone, followed by centrifugation at 3,000 rpm for 10 minutes to collect the precipitate. After dissolving the precipitate in 5 ml of a 10 mM phosphate buffer (pH 7.0), the resultant solution was dialyzed for 20 hours against 500 ml of the same buffer. The dialyzate was thereafter lyophilized to obtain 8 mg of the enzyme in a purified form (3.8 U/mg).

EXAMPLE 3

Measuring Method of Activity of Pancreatic Lipase

Composition of a reaction solution for the glycerokinase.glycerophosphate oxidase method [GK.GPO method]:

|  | Final concentration |
|---|---|
| HEPES-NaOH (pH 7.7)**** | 20 mM |
| 1,2-Dilinolein | 1.0 mM |
| Non-ionic surface active agent | 0.14% |
| Colipase | 0.2 mg/ml |
| Sodium deoxycholate | 7.0 mM |
| Sodium cholate | 3.0 mM |
| Calcium chloride | 0.7 mM |
| Ammonium chloride | 10.0 mM |
| Monoglyceride lipase of this invention | 1.0 U/ml |
| Glycerokinase | 0.5 U/ml |
| Adenosin triphosphate | 0.5 mM |
| Magnesium chloride | 0.7 mM |
| Glycerophosphate acid oxidase | 20.0 U/ml |
| TOOS | 0.02% |
| 4-Aminoantipyrine | 0.03% |
| Peroxidase | 3 U/ml |

Composition of a reaction solution for the glycerol oxidase method [GO method]:

|  | Final concentration |
|---|---|
| HEPES-NaOH (pH 7.7)**** | 20 mM |
| 1,2-Dilinolein | 1.0 mM |
| Non-ionic surface active agent | 0.14% |
| Colipase | 0.2 mg/ml |
| Sodium deoxycholate | 7.0 mM |
| Sodium cholate | 3.0 mM |
| Calcium chloride | 0.7 mM |
| Monoglyceride lipase of this invention | 1.0 U/ml |
| Glycerol oxidase | 20.0 U/ml |
| Adenosine triphosphate | 0.5 mM |
| Magnesium chloride | 0.7 mM |
| TOOS | 0.02% |
| 4-Aminoantipyrine | 0.03% |
| Peroxidase | 3 U/ml |

****As a buffer, any one of Good's various buffers BES, Bicine, DIPSO, EPPS, HEPES, HEPPSO, MOPS, POPS, TAPS, TAPSO, TES and Tricine, tris-HCl, dimethylglutaric acid, imidazole or the like may be used. Phenol may be used in lieu of TOOS.

Measurement method (1) Rate assay:

After 30 μl of human serum was added to and mixed with 1.5 ml of the reaction solution of the above composition, the absorbance was continuously recorded at 37° C. and 550 nm by means of a spectrophotometer ("Shimadzu VV=250", trade name; manufactured by Shimadzu Seisakusho Ltd.). The rate of increment of the absorbance per minute was measured after the 3rd minute. The activity of the lipase was calculated in accordance with an equation which will be given subsequently. Results are shown in Table 3 for the GP.GPO method and in Table 4 for the GO method.

TABLE 3

[GK · GPO Method]

| Sample No. | Milliabsorbance/minute | U/L |
|---|---|---|
| 1 | 4.4 | 14.4 |
| 2 | 6.5 | 21.3 |
| 3 | 5.8 | 19.0 |
| 4 | 25.9 | 84.7 |
| 5 | 36.8 | 120.4 |

TABLE 4

[GO Method]

| Sample No. | Milliabsorbance/minute | U/L |
|---|---|---|
| 1 | 4.5 | 14.7 |
| 2 | 6.3 | 20.6 |
| 3 | 5.2 | 17.0 |
| 4 | 26.4 | 86.4 |

TABLE 4-continued

| | [GO Method] | |
|---|---|---|
| Sample No. | Milliabsorbance/ minute | U/L |
| 5 | 35.9 | 117.5 |

Measurement of the activity of the lipase (U/L) = Absorbance increment (A550 nm)/min × 1.53/15.6 × 1,000/30 × 1,000
15.6: Millimolar extinction coefficient of color produced by hydrogen peroxide (cm²/μmole)
1.53: Total volume of the reaction solution (ml)
1,000/30: Conversion to ml
1,000: Conversion to l (2) End point assay:

After 50 μl of human serum was added to and mixed with 1.0 μl of the reaction solution of the same composition, they were reacted at 37° C. for 30 minutes. The reaction was then terminated with 1.0 ml of 0.5% SDS and the absorbance was measured at 550 nm (AS).

As a blank test, the above procedure was repeated with a reaction solution which was not added with 1,2-diglyceride, colipase and deoxycholic acid. The reaction solution thus served as a blank (AB).

The activity of the lipase was calculated in accordance with an equation which will be given subsequently. Results are shown in Table 5 for the GP.GPO method and in Table 6 for the GO method.

TABLE 5

| | [GK · GPO Method] | | | |
|---|---|---|---|---|
| Sample No. | AS | AB | Δ | U/AL |
| 1 | 0.189 | 0.020 | 0.169 | 14.8 |
| 2 | 0.250 | 0.015 | 0.235 | 20.6 |
| 3 | 0.213 | 0.008 | 0.205 | 17.9 |
| 4 | 0.986 | 0.014 | 0.972 | 85.2 |
| 5 | 1.307 | 0.021 | 1.286 | 112.7 |

TABLE 6

| | [GO Method] | | | |
|---|---|---|---|---|
| Sample No. | AS | AB | Δ | U/AL |
| 1 | 0.191 | 0.021 | 0.170 | 14.9 |
| 2 | 0.240 | 0.016 | 0.224 | 19.6 |
| 3 | 0.204 | 0.006 | 0.198 | 17.3 |
| 4 | 0.985 | 0.015 | 0.970 | 84.9 |
| 5 | 1.313 | 0.023 | 1.290 | 112.9 |

Measurement of the activity of the lipase (U/L) = A550 nm (AS-AB) × 2.05/15.6 × 1/30 × 1,000/50 × 1,000
15.6: Millimolar extinction coefficient of color produced by hydrogen peroxide (cm²/μmole)
1/30: Conversion to 1 minute
1,000/50: Conversion to ml
1,000: Conversion to l
2.05: Total volume of the reaction solution (ml)

EXAMPLE 4

Measurement of the monoglyceride

Composition of a reaction solution for the glycerokinase.glycerophosphate oxidase method [GK.GPO method]:

| | Final concentration |
|---|---|
| HEPES-NaOH (pH 7.7)**** | 20 mM |
| Triton X-100 | 0.1% |
| Calcium chloride | 1.0 mM |
| Monoglyceride lipase of this invention | 0.5 U/ml |
| Glycerokinase | 0.5 U/ml |
| Adenosine triphosphate | 1.0 mM |
| Glycerophosphate oxidase | 5.0 U/ml |
| TOOS | 0.02% |
| 4-Aminoantipyrine | 0.03% |
| Peroxidase | 3 U/ml |

Composition of a reaction solution for the glycerol oxidase method [GO method]:

| | Final concentration |
|---|---|
| HEPES-NaOH (pH 7.7)**** | 20 mM |
| Triton X-100 | 0.1% |
| Calcium chloride | 1.0 mM |
| Monoglyceride lipase of this invention | 0.5 U/ml |
| Glycerol oxidase | 5.0 U/ml |
| TOOS | 0.02% |
| 4-Aminoantipyrine | 0.03% |
| Peroxidase | 3 U/ml |

****As a buffer, any one of Good's various buffers BES. Bicine. DIPSO. EPPS. HEPES. HEPPSO. MOPS. POPS. TAPS. TAPSO. TES and Tricine. tris-HCl. dimethylglutaric acid. imidazole or the like may be used. Phenol may be used in lieu of TOOS.

MEASUREMENT METHOD

Figure 6:
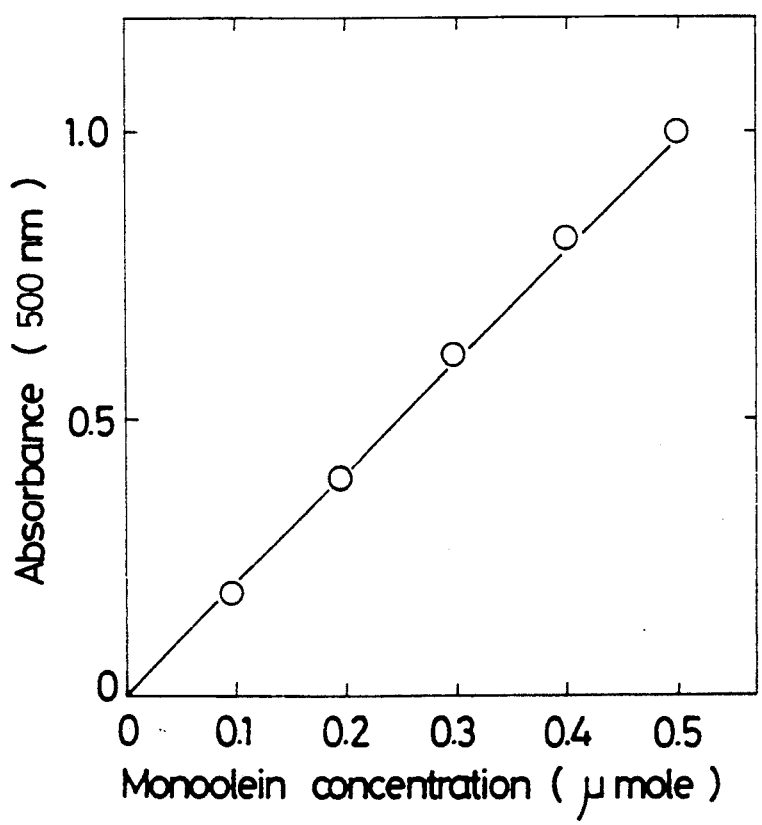
FIG. 6 shows a calibration curve for monoglyceride.

To 3.0 ml portions of the respective reaction mixture, 50 μl portions of samples containing 0–0.5 μmole of the monoglyceride (1-monoolein) were added. After conducting a color-producing reaction at 37° C. for 15 minutes by the GK.GPO method, the absorbance levels were separately measured at 500 nm. As illustrated in FIG. 6, a straight line indicative of a proportional correlation was obtained up to the monoglyceride amount of 0.5 μmole. Further, the GO method also gave a straight line indicative of a proportional correlation up to the monoglyceride amount of 0.5 μmole.

We claim:

1. An analytical method for measuring the monoglyceride content of a sample solution, comprising contacting said sample solution with a monoglyceride lipase that is capable of the enzymatic hydrolysis of monoglycerides, but not diglycerides or triglycerides, according to the following equation:

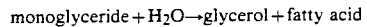

monoglyceride + H$_2$O → glycerol + fatty acid to enzymatically hydrolyze said monoglyceride of said sample solution, and measuring the amount of either the glycerol or the fatty acid formed by said enzymatic hydrolysis.

2. The analytical method as claimed in claim 1, wherein the monoglyceride in the sample solution being measured is a monoglyceride liberated by the reaction of pancreatic lipase with a 1,2-diglyceride in the sample solution.

3. The analytical method as claimed in claim 1, wherein the amount of glycerol is measured by reacting glycerol oxidase or glycerokinase and glycerophosphate acid oxidase with the formed glycerol, and measuring the amount of hydrogen peroxide formed thereby.

4. The analytical method as claimed in claim 3, wherein for the measurement of the amount of hydrogen peroxide, a dye composition containing at least one chromogen reagent capable of undergoing a colorimetric change in the presence of hydrogen peroxide is added to the hydrogen peroxide formed.

5. The analytical method as claimed in claim 4, wherein the dye composition contains a peroxidase.

6. The analytical method as claimed in claim 5, wherein the peroxidase is used in an amount of 0.5-10 U.

7. The analytical method as claimed in claim 4, wherein the chromogen reagent of the dye composition comprises 4-aminoantipyrine, a peroxidase and either N-ethyl-N-(2-hydroxy-3-sulfolpropyl)-metha-toluidine or phenol.

8. The analytical method as claimed in claim 1, wherein the measurement of the amount of fatty acid formed by said enzymatic hydrolysis comprises the following reaction steps (a), (b), (c), (e) and (f):
(a) converting the fatty acid to acyl-CoA,
(b) converting the acyl-CoA to dehydroacyl-CoA,
(c) converting the dehydroacyl-CoA to hydroxyacyl-CoA,
(d) converting the hydroxyacyl-CoA to ketoacyl-CoA,
(e) converting the ketoacyl-CoA to acyl-CoA; and
(f) measuring a change in the amount of reaction product acyl-CoA of step (a) and reaction product acyl-CoA of step (e), the latter having a carbon content smaller by 2.

9. The analytical method as claimed in claim 8, wherein in the reaction steps (a), (b), (c), (d) and (e), the reaction step (a) is based on the fatty acid, CoASH, ATP or GTP and the activity of acyl-CoA.synthetase, the reaction step (b) is based on the acyl-CoA and oxygen as well as the activity of acyl-CoA.oxidase, the reaction step (c) is based on the dehydroacyl-CoA and water as well as the activity of enoyl-CoA.hydratase, the reaction step (d) is based on the hydroxyacyl-CoA and NAD as well as the activity of 3-hydroxyacyl-CoA.dehydrogenase, and the reaction step (e) is based on the ketoacyl-CoA and CoASH as well as the activity of 3-ketoacyl-CoA.thiolase.

10. The analytical method as claimed in claim 8, wherein the step (f) of measuring the change in amount of the reaction product comprises quantitatively analyzing reduced NAD formed.

11. The analytical method as claimed in claim 10, wherein the quantitative analysis of the resultant reduced NAD is carried out by spectrophotometry around 320-360 nm which are absorption wavelengths not characteristic to NAD but characteristic to reduced NAD.

12. The anlaytical method as claimed in claim 10, wherein the quantitative analysis of the resultant reduced NAD is carried out based on the production of a color by a chromogen which has receptivity for the hydrogen atoms of reduced NAD.

13. The analytical method as claimed in claim 12, wherein the chromogen having receptivity for the hydrogen atoms of reduced NAD is a composition comprising, diaphorase and a water-soluble tetrazolium salt.

14. The analytical method as claimed in claim 1, wherein said monoglyceride lipase has been obtained by culturing the monoglyceride lipase-producing microorganisms *Bacillus stearothermophilus* H-165 (FERM BP-1673) and recovering the monoglyceride lipase from the resulting culture.

15. An analytical method for determining the activity of pancreatic lipase in a sample solution, comprising reacting pancreatic lipase in a said sample solution with a 1,2-diglyceride to liberate monoglyceride in said sample solution, reacting said liberated monoglyceride with a monoglyceride lipase that is capable of the enzymatic hydrolysis of monoglycerides, but not diglycerides or triglycerides, according to the follow equation:

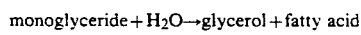

monoglyceride + $H_2O$ → glycerol + fatty acid to enzymatically hydrolyze said monoglyceride of said sample solution, and measuring the amount of either one of glycerol and fatty acid formed by said enzymatic hydrolysis.

16. The analytical method as claimed in claim 15, wherein the amount of glycerol is measured by reacting glycerol oxidase or glycerokinase and glycerophosphate acid oxidase with the formed glycerol, and measuring the amount of hydrogen peroxide formed thereby.

17. The analytical method as claimed in claim 16, wherein for the measurement of the amount of hydrogen peroxide, a dye composition containing at least one chromogen reagent capable of undergoing a colorimetric change in the presence of hydrogen peroxide is added to the hydrogen peroxide formed.

18. The analytical method as claimed in claim 17, wherein the dye composition contains a peroxidase.

19. The analytical method as claimed in claim 18, wherein the peroxidase is used in an amount of 0.5-10 U.

20. The analytical method as claimed in claim 17, wherein the chromogen reagent of the dye composition comprises 4-aminoantipyrine, a peroxidase and either N-ethyl-N-(2-hydroxy-3-sulfopropyl-metha-toluidine or phenol.

21. The analytical method as claimed in claim 15, wherein said monoglyceride lipase has been obtained by culturing the monoglyceride lipase-producing microorganism *Bacillus stearothermophilus* H-165 (FERM BP-1673) and recovering the monoglyceride lipase from the resulting culture.

* * * * *